US009540282B2

(12) United States Patent
Saitou et al.

(10) Patent No.: US 9,540,282 B2
(45) Date of Patent: Jan. 10, 2017

(54) GAS SENSOR ELEMENT AND ITS MANUFACTURING METHOD

(71) Applicant: DENSO CORPORATION, Kariya, Aichi-pref. (JP)

(72) Inventors: Masami Saitou, Nagoya (JP); Namitsugu Fujii, Yokkaichi (JP); Norikazu Kajiyama, Chiryu (JP)

(73) Assignee: DENSO CORPORATION, Kariya (JP)

( * ) Notice: Subject to any disclaimer, the term of this patent is extended or adjusted under 35 U.S.C. 154(b) by 756 days.

(21) Appl. No.: 13/836,360

(22) Filed: Mar. 15, 2013

(65) Prior Publication Data

US 2013/0240354 A1   Sep. 19, 2013

(30) Foreign Application Priority Data

Mar. 16, 2012 (JP) .................. 2012-060513

(51) Int. Cl.
*G01N 27/407* (2006.01)
*C04B 35/10* (2006.01)
(Continued)

(52) U.S. Cl.
CPC .............. *C04B 35/10* (2013.01); *B28B 1/008* (2013.01); *B28B 1/24* (2013.01); *C04B 35/48* (2013.01);
(Continued)

(58) Field of Classification Search
CPC ............ B28B 1/24; B28B 1/008; C04B 35/48; C04B 37/001; C04B 35/10; C04B 2235/6022; G01N 27/407
See application file for complete search history.

(56) References Cited

U.S. PATENT DOCUMENTS 4,908,119 A * 3/1990 Saito ................. G01N 27/4077
204/426
4,980,042 A 12/1990 Shiomi et al.
(Continued)

FOREIGN PATENT DOCUMENTS

CN    101281160    10/2008
JP    S53-139595   12/1978
(Continued)

OTHER PUBLICATIONS

Office Action (2 pages) dated Mar. 25, 2015, issued in corresponding Japanese Application No. 2012-060513 and English translation (2 pages).
(Continued)

*Primary Examiner* — Gurpreet Kaur
(74) *Attorney, Agent, or Firm* — Nixon & Vanderhye P.C.

(57) ABSTRACT

A gas sensor element includes a basal body, at least one solid electrolyte portion and a pair of electrodes. The basal body has a bottomed tubular shape and is made of an electrically insulative ceramic material. The basal body has a side wall and a bottom wall. The at least one solid electrolyte portion is formed in the bottom wall or the side wall of the basal body. The pair of electrodes are opposed to each other with the at least one solid electrolyte portion interposed therebetween. The difference in surface level between the basal body and the at least one solid electrolyte portion at a boundary therebetween is less than or equal to 30 μm.

2 Claims, 17 Drawing Sheets

(51) Int. Cl.
*B28B 1/24* (2006.01)
*C04B 35/48* (2006.01)
*C04B 37/00* (2006.01)
*B28B 1/00* (2006.01)

(52) U.S. Cl.
CPC .......... *C04B 37/001* (2013.01); *G01N 27/407* (2013.01); *C04B 2235/6022* (2013.01); *C04B 2237/343* (2013.01); *C04B 2237/348* (2013.01); *C04B 2237/765* (2013.01); *C04B 2237/78* (2013.01)

(56) References Cited

U.S. PATENT DOCUMENTS

| | | | |
|---|---|---|---|
| 5,935,399 A | 8/1999 | Tanaka et al. | |
| 6,174,448 B1* | 1/2001 | Das | C23C 8/80 134/6 |
| 6,174,489 B1* | 1/2001 | Kobayashi | G01N 27/4073 264/618 |
| 2005/0189222 A1* | 9/2005 | Tsuzuki | B28B 1/008 204/424 |
| 2006/0219554 A1 | 10/2006 | Mori et al. | |
| 2011/0017596 A1* | 1/2011 | Kamiya | G01N 27/4078 204/424 |
| 2011/0154889 A1* | 6/2011 | Stafford | A61B 19/0264 73/61.59 |
| 2012/0043131 A1* | 2/2012 | Christov | B29C 45/14073 174/521 |

FOREIGN PATENT DOCUMENTS

| | | |
|---|---|---|
| JP | S54-118293 | 9/1979 |
| JP | S61-272649 | 12/1986 |
| JP | S62-222159 | 9/1987 |
| JP | 63-061160 | 3/1988 |
| JP | H03-138559 | 6/1991 |
| JP | 04-049003 | 2/1992 |
| JP | H09-304337 | 11/1997 |
| JP | H11-183430 | 7/1999 |
| JP | 2006-308545 | 11/2006 |
| JP | 2007-218741 | 8/2007 |
| JP | 2007-278941 | 10/2007 |
| JP | 2010-145214 | 7/2010 |

OTHER PUBLICATIONS

Office Action (2 pages) dated Nov. 26, 2013, issued in corresponding Japanese Application No. 2012-060513 and English translation (2 pages).

Office Action (1 page) dated Sep. 2, 2014, issued in corresponding Japanese Application No. 2012-060513 and English translation (2 pages).

Office Action (6 pages) dated Jul. 30, 2014, issued in corresponding Chinese Application No. 201310082570.5 and English translation (7 pages).

Office Action (1 page) dated Aug. 25, 2015 issued in corresponding Japanese Application No. 2012-060513 and English translation (1 page).

* cited by examiner

GAS SENSOR ELEMENT AND ITS MANUFACTURING METHOD

CROSS-REFERENCE TO RELATED APPLICATION

This application is based on and claims priority from Japanese Patent Application No. 2012-60513, filed on Mar. 16, 2012, the content of which is hereby incorporated by reference in its entirety into this application.

BACKGROUND

1. Technical Field

The present invention relates to a gas sensor element that includes a basal body having a bottomed tubular shape and made of an electrically insulative ceramic material, a solid electrolyte portion and a pair of electrodes, and to a method of manufacturing the gas sensor element.

2. Description of Related Art

There are known gas sensor elements that are employed in, for example, lambda sensors or A/F (Air/Fuel) ratio sensors to detect the concentration of oxygen in the exhaust gas from an internal combustion engine of a motor vehicle.

More specifically, lambda sensors are generally configured to detect the concentration of oxygen in the exhaust gas based on an electromotive force outputted from the gas sensor element; the electromotive force represents the difference in oxygen concentration between the exhaust gas and a reference gas (e.g., air). On the other hand, A/F ratio sensors are generally configured to detect the concentration of oxygen in the exhaust gas based on a limit current outputted from the gas sensor element; the limit current also represents the difference in oxygen concentration between the exhaust gas and the reference gas. In addition, the A/F ratio sensors are generally configured to further determine the A/F ratio of air-fuel mixture supplied to the engine based on the detected concentration of oxygen in the exhaust gas.

Moreover, the known gas sensor elements are generally configured to include a solid electrolyte body and a pair of measurement and reference electrodes. The solid electrolyte body is made, for example, of zirconia partially stabilized by yttria. The measurement and reference electrodes are made of, for example, platinum and respectively provided on opposite surfaces of the solid electrolyte body so as to be respectively exposed to the exhaust gas (i.e., the measurement gas or the gas to be measured) and the air (i.e., the reference gas). In addition, on the measurement electrode, there is further provided a protective layer in those gas sensor elements which are used in lambda sensors and a diffusion-resistant layer in those gas sensor elements which are used in A/F ration sensors.

Furthermore, the known gas sensor elements generally have either a plate shape or a bottomed tubular shape.

More specifically, the plate-shaped gas sensor elements are generally formed by laminating a solid electrolyte layer and insulating layers. Therefore, it is easy to manufacture the plate-shaped gas sensor elements. Further, it is possible to laminate a heater layer together with the solid electrolyte and insulating layers, thereby easily heating the solid electrolyte layer in operation. However, due to the plate-like shape, corner portions are formed at ends of the gas sensor elements. Consequently, with the corner portions, the gas sensor elements may be easily damaged by, for example, thermal shock caused by water generated in the exhaust pipe.

On the other hand, for the bottomed tubular gas sensor elements, it is possible to configure a bottom surface thereof as a curved surface. Consequently, with the curved bottom surface, it is possible to alleviate thermal shock caused by water generated in the exhaust pipe, thereby preventing the gas sensor elements from being damaged by the water.

Moreover, to minimize the manufacturing cost of the gas sensor elements, it is desired to minimize the amount of solid electrolyte used in the gas sensor elements.

To meet the above desire, Japanese Unexamined Patent Application Publication No. H3-138559 discloses a gas sensor element which includes a hollow cylindrical heater body. In the outer surface of the heater body, there is formed a groove so as to communicate with the hollow space formed in the heater body via a through-hole. A solid electrolyte layer is formed on the outer surface of the heater body so as to cross over the opening of the groove.

With the above configuration, however, there is a difference in level (or height) between the outer surface of the heater body and the outer surface of the solid electrolyte layer. Therefore, during the firing process of the gas sensor element or when thermal shock is applied to the gas sensor element due to water contained in the exhaust gas, stress concentration may occur at the boundary between the heater body and the solid electrolyte layer due to the difference in surface level therebetween. Consequently, damage may be caused to the gas sensor element, such as causing cracks to occur in the heater body or in the solid electrolyte layer or causing electrode lead wires of the gas sensor element to be broken.

SUMMARY

According to an exemplary embodiment, there is provided a gas sensor element which includes a basal body, at least one solid electrolyte portion and a pair of electrodes. The basal body has a bottomed tubular shape and is made of an electrically insulative ceramic material. The basal body has a side wall and a bottom wall. The at least one solid electrolyte portion is formed in the bottom wall or the side wall of the basal body. The pair of electrodes are opposed to each other with the at least one solid electrolyte portion interposed therebetween. The difference in surface level between the basal body and the at least one solid electrolyte portion at a boundary therebetween is less than or equal to 30 μm.

With such a small difference, during the firing process of the gas sensor element or when thermal shock is applied to the gas sensor element due to water contained in the measurement gas (i.e., the gas to be measured by the gas sensor element), stress concentration can be prevented from occurring at the boundary between the basal body and the solid electrolyte portion. As a result, it is possible to prevent cracks from occurring in the gas sensor element.

Moreover, with the bottomed tubular shape of the basal body, the gas sensor element can be configured to have no corner portion at the measurement gas-side end thereof. Consequently, it is possible to prevent cracks from occurring in the gas sensor element due to stress concentration at a corner portion thereof. In addition, it is also possible to prevent the gas sensor element from being damaged during the assembly thereof with other components due to collision of a corner portion thereof against the other components.

To more reliably prevent cracks from occurring in the gas sensor element, the difference in surface level between the basal body and the at least one solid electrolyte portion at the boundary therebetween is preferably equal to or less than 10 μm, and more preferably equal to or less than 5 μm.

It is preferable that the bottom and side walls of the basal body are connected with each other via a curved boundary portion therebetween. In this case, it is possible to prevent stress concentration from occurring at the boundary portion between the side wall and bottom wall of the basal body, thereby more reliably preventing cracks from occurring in the gas sensor element.

It is also preferable that the major component of the at least one solid electrolyte portion is partially-stabilized zirconia. In this case, it is possible to secure high sensitivity of the gas sensor element.

It is also preferable that the major component of the electrically insulative ceramic material, of which the basal body is made, is alumina. In this case, it is possible to secure both high heat conductivity and high electrical insulating properties of the basal body.

According to the exemplary embodiment, there is also provided a method of manufacturing the gas sensor element. The method includes the steps of: (1) shaping a first clay, which is provided for forming the basal body, into the shape of the basal body so that at least one void space is formed in the shaped first clay; (2) shaping a second clay, which is provided for forming the at least one solid electrolyte portion, into the shape of the at least one solid electrolyte portion by filling the second clay into the at least one void space formed in the shaped first clay; (3) firing both the shaped first and second clays together to form the basal body and the at least one solid electrolyte portion; and (4) forming the pair of electrodes respectively on opposite sides of the at least one solid electrolyte portion.

With the above method, the basal body and the at least one solid electrolyte portion can be integrally formed into one piece so that the at least one solid electrolyte portion is included in the bottom wall or the side wall of the basal body. Moreover, since the second clay is shaped by being filled into the at least one void space previously formed in the first clay, it is possible to realize such a small difference in surface level between the basal body and the at least one solid electrolyte portion at the boundary therebetween as described above.

In addition, the first clay for forming the basal body may be obtained by mixing powder of the electrically insulative ceramic material, an organic binder, a dispersant and water. Similarly, the second clay for forming the at least one solid electrolyte portion may be obtained by mixing powder of a solid electrolyte material, an organic binder, a dispersant and water.

It is preferable that both the first and second clays are shaped by injection molding using a die assembly. In this case, it is possible to accurately shape both the first and second clays, thereby reliably suppressing the difference in surface level between the basal body and the at least one solid electrolyte portion at the boundary therebetween.

Further, preferably, the die assembly has a cavity formed therein; the cavity has the shape of the basal body. In the first clay shaping step, the first clay is filled into the cavity with at least one portion of the cavity occupied by a movable member. In the second clay shaping step, the second clay is filled into the at least one void space which is formed in the shaped first clay by removing the movable member to vacate the at least one portion of the cavity. In this case, it is possible to easily form the basal body and the at least one solid electrolyte portion integrally so that the at least one solid electrolyte portion is included in the bottom wall or the side wall of the basal body.

It is also preferable that the method further includes, after the second clay shaping step and before the firing step, a step of degreasing both the shaped first and second clays. In this case, it is possible to remove organic components included in the shaped first and second clays before firing them.

BRIEF DESCRIPTION OF THE DRAWINGS

The present invention will be understood more fully from the detailed description given hereinafter and from the accompanying drawings of exemplary embodiments, which, however, should not be taken to limit the invention to the specific embodiments but are for the purpose of explanation and understanding only.

In the accompanying drawings.

DESCRIPTION OF EMBODIMENTS

Figure 1:
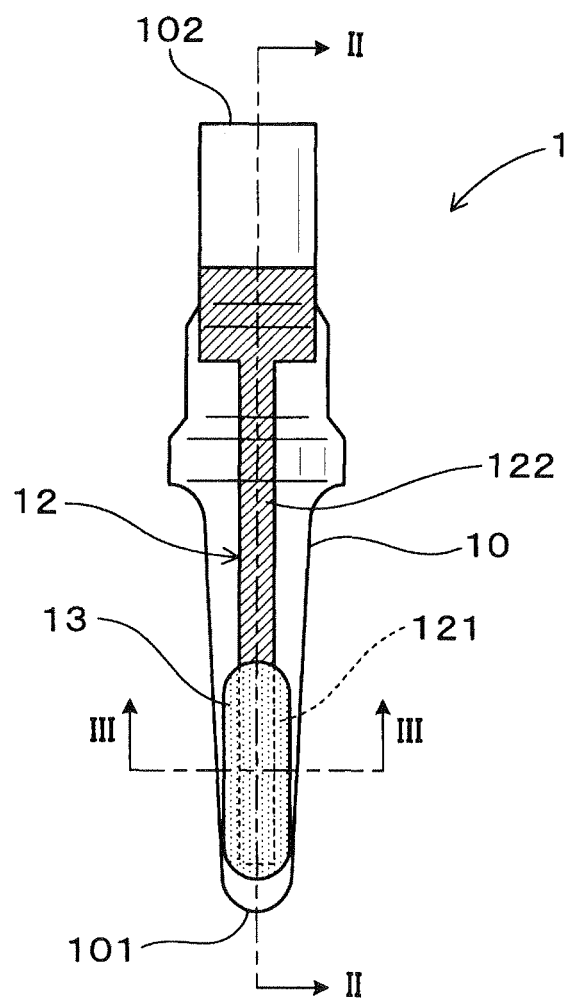
FIG. 1 is a side view of a gas sensor element according to a first embodiment.

Exemplary embodiments will be described hereinafter with reference to FIGS. 1-25. It should be noted that for the sake of clarity and understanding, identical components having identical functions throughout the whole description have been marked, where possible, with the same reference numerals in each of the figures and that for the sake of avoiding redundancy, descriptions of the identical components will not be repeated.

First Embodiment

FIGS. 1-4 together show the overall configuration of a gas sensor element 1 according to a first embodiment. The gas sensor element 1 is designed to be used in detecting the concentration of a specific component in a gas to be measured (to be simply referred to as a measurement gas hereinafter).

As shown in the figures, the gas sensor element 1 includes a basal body 10, a solid electrolyte portion 103 and a pair of reference and measurement electrodes 11 and 12. The basal body 10 has a bottomed tubular shape (or a cup shape) and is made of an electrically insulative ceramic material. That is, one end 101 of the basal body 10 is closed while the other end 102 is open. The basal body 10 has a side wall 104 and a round bottom wall 108. The solid electrolyte portion 103 is integrally formed with the basal body 10 so as to be embedded in part of the side wall 104 of the basal body 10. The reference and measurement electrodes 11 and 12 are opposed to each other with the solid electrolyte portion 103 interposed therebetween. The difference in surface level (or surface height) between the basal body 10 and the solid electrolyte portion 103 at the boundary 105 therebetween is specified to be less than or equal to 30 μm.

The detailed configuration of the gas sensor element 1 according to the present embodiment will be described hereinafter.

The basal body 10 contains, for example, alumina ($Al_2O_3$) as its major component. More specifically, the percentage content of alumina in the basal body 10 is 90 mass % or higher. Moreover, the basal body 10 may further contain, for example, at least one of zirconia ($ZrO_2$), yttria ($Y_2O_3$), magnesia (MgO), calcia (CaO) and silica ($SiO_2$) in addition to alumina.

The basal body 10 has the bottomed tubular shape so that there is formed a hollow space in the basal body 10. In addition, though not graphically shown, a rod-shaped heater may be arranged in the hollow space of the basal body 10 to heat the solid electrolyte portion 103. Consequently, with the heater, it is possible to reduce the time required for the solid electrolyte portion 103 to become able to conduct oxygen ions, thereby ensuring prompt activation of the solid electrolyte portion 103.

Figure 2:
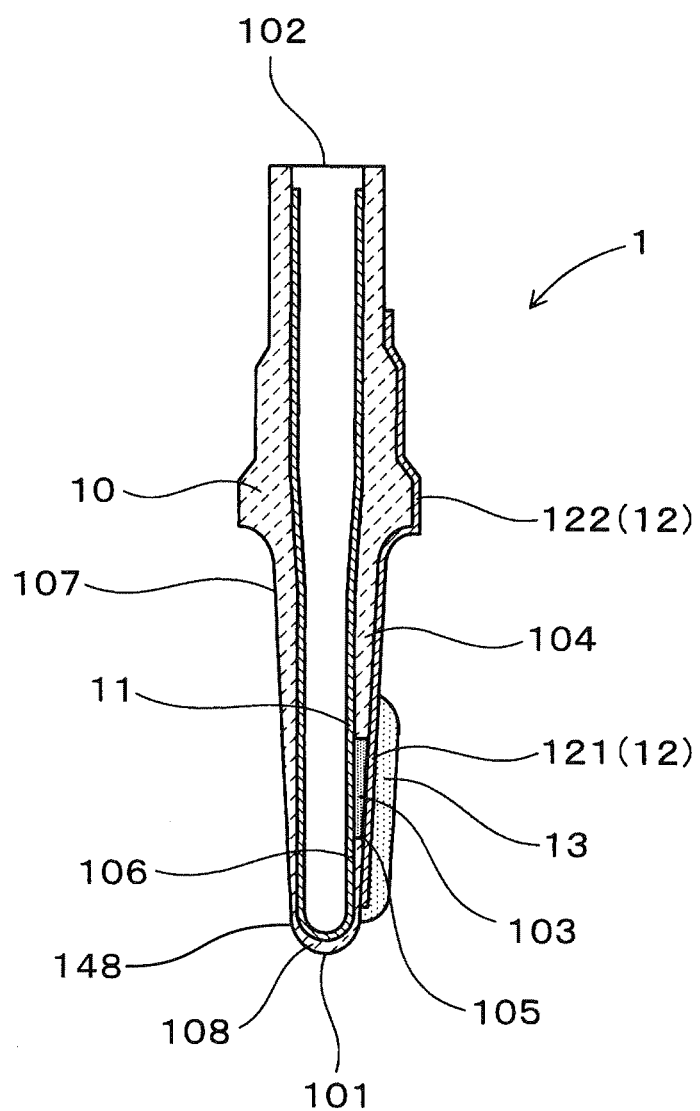
FIG. 2 is a cross-sectional view of the gas sensor element taken along the line II-II in FIG. 1.
Figure 3:
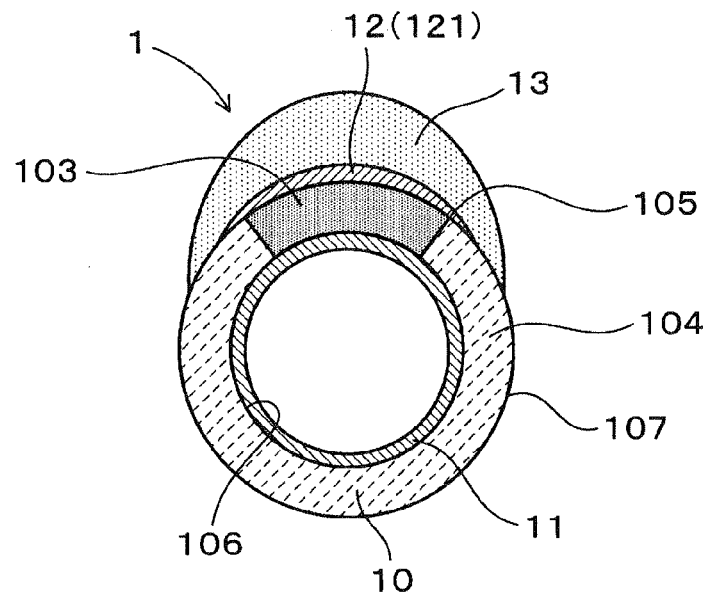
FIG. 3 is a cross-sectional view of the gas sensor element taken along the line III-III in FIG. 1.

In the present embodiment, as shown in FIG. 2, the side wall 104 and bottom wall 108 of the basal body 10 are connected with each other via a curved boundary portion 148 therebetween.

The solid electrolyte portion 103 contains, for example, zirconia as its major component. The solid electrolyte portion 103 also contains 4-8 mol % yttria to partially stabilize zirconia. In other words, the solid electrolyte portion 103 contains the partially-stabilized zirconia as its major component. Moreover, the solid electrolyte portion 103 may further contain, for example, at least one of alumina, silica, magnesia and calcia in addition to zirconia and yttria.

The solid electrolyte portion 103 is integrally formed with the basal body 10 by being fired together with the basal body 10. The solid electrolyte portion 103 is embedded in the side wall 104 of the basal body 10 so as to replace part of the side wall 104. In addition, the solid electrolyte portion 103 is positioned close to the closed end 101 of the basal body 10.

In the present embodiment, the difference in surface level between the basal body 10 and the solid electrolyte portion 103 at the boundary 105 therebetween is 3 μm at most on both the internal surface 106 and external surface 107 of the basal body 10. In other words, there is almost no difference in surface level between the basal body 10 and the solid electrolyte portion 103 at the boundary 105 therebetween.

The reference and measurement electrodes 11 and 12 are made of an electrically conductive metal, such as platinum. The reference and measurement electrodes 11 and 12 are respectively formed on opposite sides of the solid electrolyte portion 103 so as to have the solid electrolyte portion 103 interposed therebetween. More specifically, the reference electrode 11 is formed on the internal surface 106 of the basal body 10 so as to cover almost the whole of the internal surface 106 as well as the solid electrolyte portion 103. On the other hand, the measurement electrode 12 is formed on the external surface 107 of the basal body 10 so as to have an electrode portion 121 formed on the solid electrolyte portion 103 and a lead portion 122 extending from the electrode portion 121 toward the open end 102 of the basal body 10. In addition, in operation of the gas sensor element 1, the reference electrode 11 is exposed to a reference gas, while the measurement electrode 12 is exposed to the measurement gas.

In the present embodiment, the gas sensor element 1 further includes a porous protective layer 13 that is formed on the measurement electrode 12 so as to completely cover and thereby protect the electrode portion 121 of the measurement electrode 12 from poisoning substances contained in the measurement gas. The porous protective layer 13 is made of a refractory metal oxide, such as $MgO \cdot Al_2O_3$ spinel, and has a thickness (maximum thickness) of 300 μm on the electrode portion 121.

In the present embodiment, the gas sensor element 1 is configured to be used in a lambda sensor for detecting the concentration of oxygen in the exhaust gas from an internal combustion engine of a motor vehicle.

More specifically, the gas sensor element 1 is to be inserted in an exhaust pipe of the engine from the closed end 101 thereof. In operation, the reference electrode 11 formed on the internal surface 106 of the basal body 10 is exposed to air (i.e., the reference gas) which is introduced into the hollow space of the basal body 10 from the open end 102 thereof, while the measurement electrode 12 formed on the external surface 107 of the basal body 10 is exposed to the exhaust gas (i.e., the measurement gas) flowing in the exhaust pipe. The solid electrolyte portion 103 and the reference and measurement electrodes 11 and 12 that are respectively formed on opposite surfaces of the solid electrolyte portion 103 together make up an electrochemical cell. Consequently, depending on the difference in oxygen concentration between air and the exhaust gas, an electric voltage is created between the reference and measurement electrodes 11 and 12. As a result, it is possible to determine the concentration of oxygen in the exhaust gas based on the electric voltage outputted from the gas sensor element 1.

Next, a method of manufacturing the gas sensor element 1 according to the present embodiment will be described.

The method includes a first shaping step, a second shaping step, a degreasing step, a firing step and an electrode forming step. In the first shaping step, a first clay 18 for forming the basal body 10 is shaped into the bottomed tubular shape of the basal body 10 so that a void space 201 is formed in the shaped first clay 18 at a position corresponding to the solid electrolyte portion 103 (see FIGS. 6 and 7). In the second shaping step, a second clay 19 for forming the solid electrolyte portion 103 is filled into the void space 201, thereby being shaped into the shape of the solid electrolyte portion 103 (see FIGS. 8 and 9). In the degreasing step, a green body 100 obtained by the first and second shaping steps is degreased (see FIG. 10). In the firing step, the degreased green body 100 is fired to form the basal body 10 and the solid electrolyte portion 103. In the electrode forming step, the reference and measurement electrodes 11 and 12 are respectively formed on the internal and external surfaces 106 and 107 of the basal body 10 (see FIGS. 1-3).

The method of manufacturing the gas sensor element 1 according to the present embodiment will be described in more detail hereinafter.

In the first shaping step, alumina powder, paraffin resin, styrene-butadiene copolymer resin and stearic acid are mixed together by adding pure water thereto and being heated, forming the first clay 18.

Figure 5:
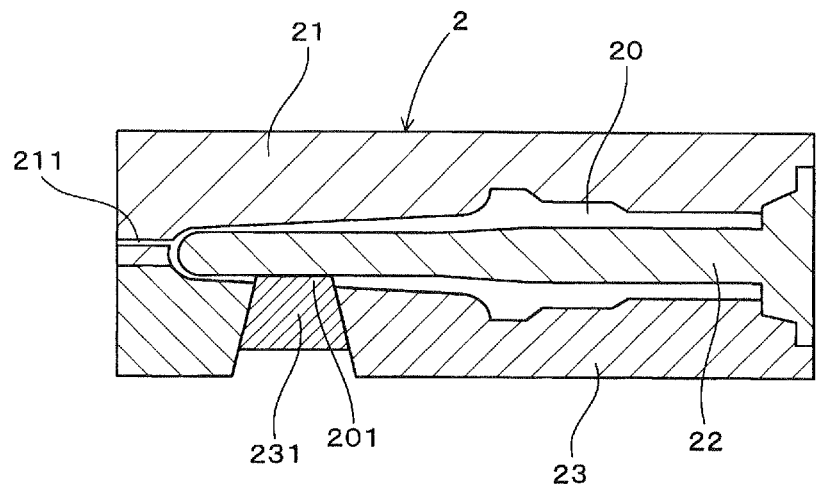
FIG. 5 is a cross-sectional view illustrating the configuration of a die assembly used in manufacturing the gas sensor element, wherein a portion of a cavity formed in the die assembly is occupied by a first movable die.

Then, as shown in FIG. 5, an injection molding die assembly 2 is prepared which has a cavity 20 formed therein; the cavity 20 has the bottomed tubular shape of the basal body 10. The die assembly 2 consists of an upper die 21, an intermediate die 22, a lower die 23 and a movable die 231, all of which are detachable from each other. In the upper die 21, there is formed an injection port 211 for injecting the first clay 18 into the cavity 20 that is defined by the upper, intermediate and lower dies 21-23. In the lower die 23, there is formed an opening of the cavity 20 at a position corresponding to the solid electrolyte portion 103. The movable die 231 is inserted into the cavity 20, through the opening formed in the lower die 23, to occupy a portion 201 of the cavity 20 where the solid electrolyte portion 103 is to be formed.

Figure 6:
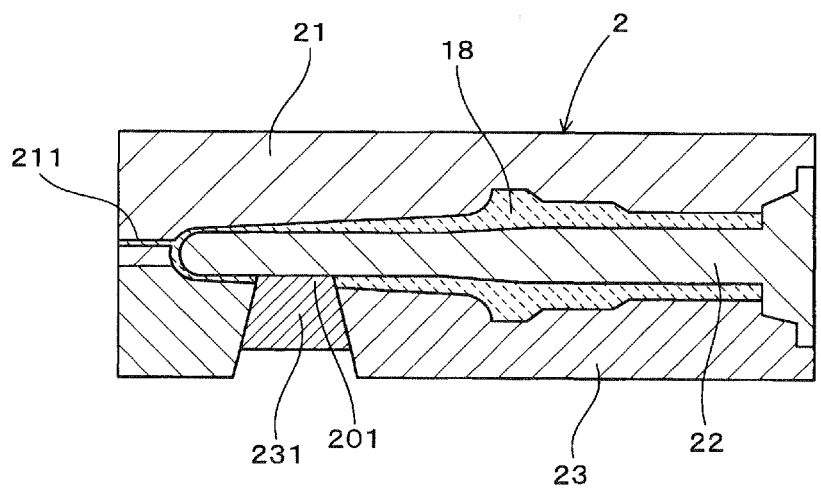
FIG. 6 is a cross-sectional view illustrating a state where the cavity formed in the die assembly has been filled with a first clay for forming the basal body with the portion of the cavity occupied by the first movable die.

Thereafter, as shown in FIG. 6, a first injection molding is performed by injecting the first clay 18 into the cavity 20 via the injection port 211 to fill the cavity 20. Consequently, the first clay 18 is shaped into the bottomed tubular shape of the basal body 10.

Figure 7:
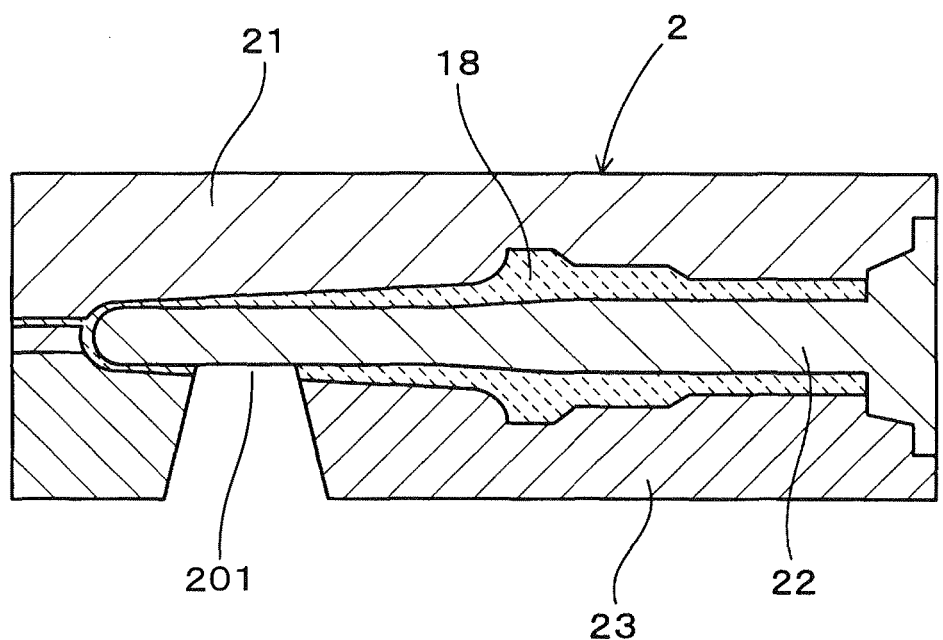
FIG. 7 is a cross-sectional view illustrating another state where the first movable die has been removed to vacate the portion of the cavity after the cavity is filled with the first clay.

Further, as shown in FIG. 7, the movable die 231 is removed from the lower die 23 to vacate the portion 201 of the cavity 20, thereby forming the void space 201 in the shaped first clay 18.

In the second shaping step, zirconia powder, yttria powder, paraffin resin, styrene-butadiene copolymer resin and stearic acid are mixed together by adding pure water thereto and being heated, forming the second clay 19.

Figure 8:
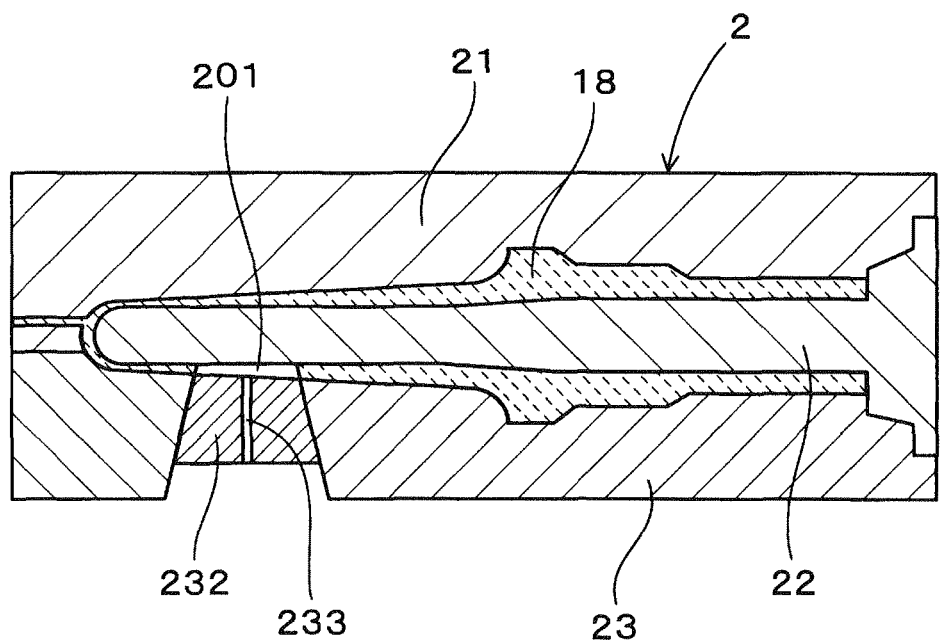
FIG. 8 is a cross-sectional view illustrating yet another state where a second movable die has been inserted in an opening of the die assembly which communicates with the portion of the cavity.

Then, as shown in FIG. 8, another movable die 232 is inserted into the opening formed in the lower die 23 without occupying the void space 201 formed in the shaped first clay 18. In the movable die 232, there is formed an injection port 233 for injecting the second clay 19 into the void space 201.

Figure 9:
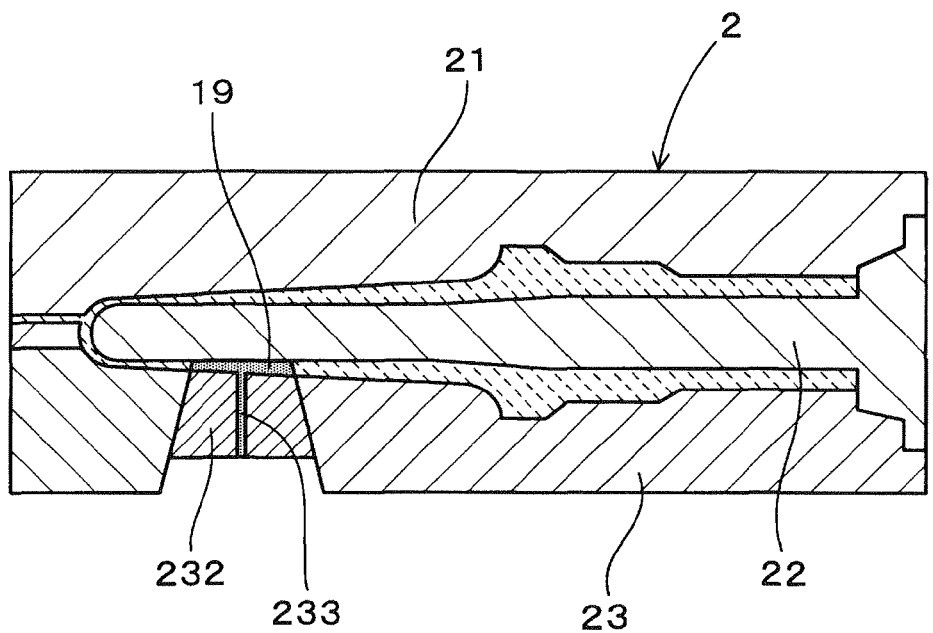
FIG. 9 is a cross-sectional view illustrating still another state where the portion of the cavity has been filled with a second clay for forming the solid electrolyte portion.

Thereafter, as shown in FIG. 9, a second injection molding is performed by injecting the second clay 19 into the void space 201 formed in the shaped first clay 18 via the injection port 233 to fill the void space 201. Consequently, the second clay 19 is shaped into the shape of the solid electrolyte portion 103.

Figure 10:
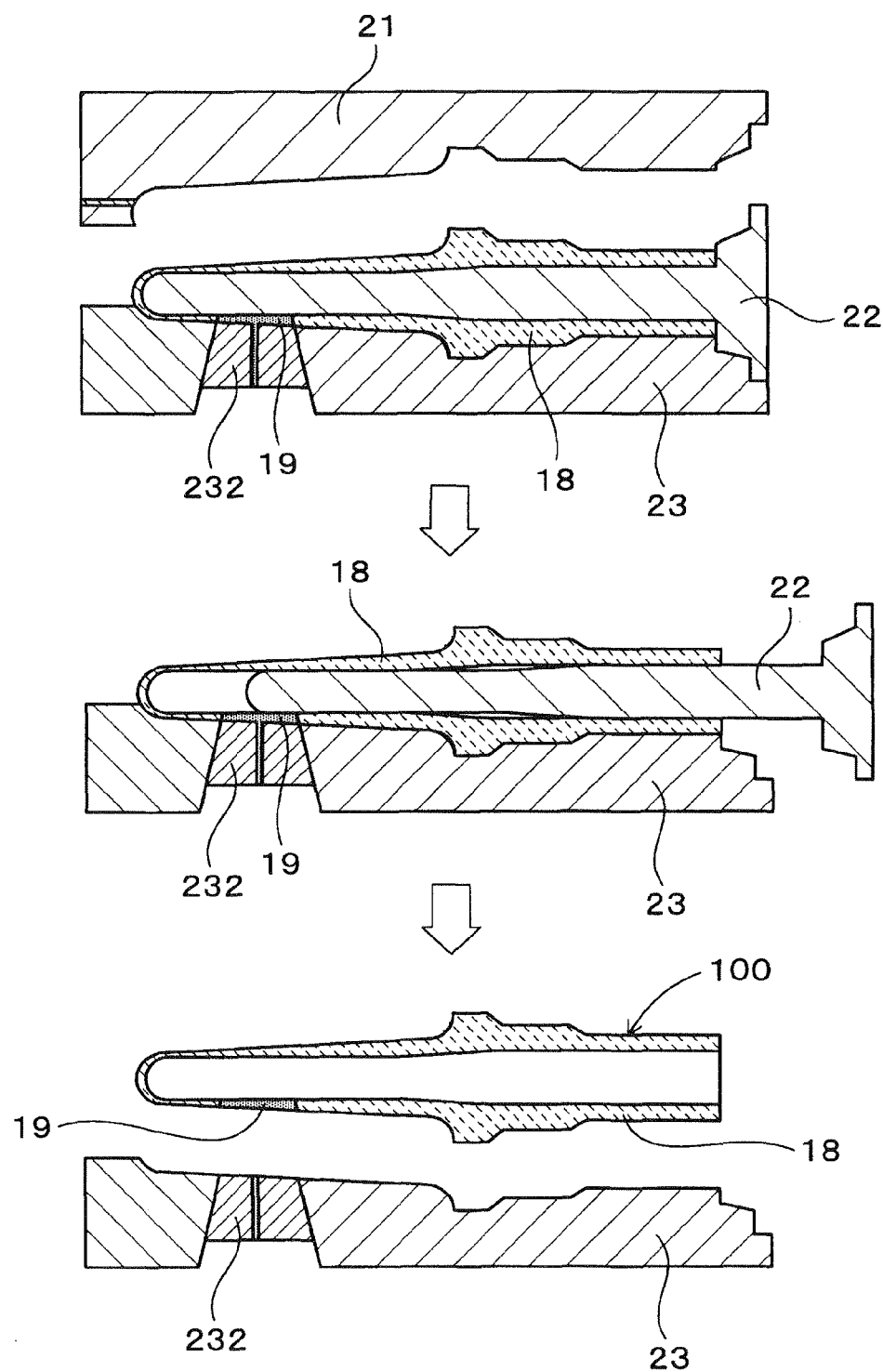
FIG. 10 is a schematic view illustrating the removal of a green body from the die assembly, the green body consisting of the shaped first and second clays.

Further, as shown in FIG. 10, the shaped first and second clays 18 and 19 are removed from the dies 21-23 and 232. As a result, the green body 100 is obtained which includes the first clay 18 shaped into the bottomed tubular shape of the basal body 10 and the second clay 19 embedded in the first clay 18 so as to form the solid electrolyte portion 103.

Figure 4:
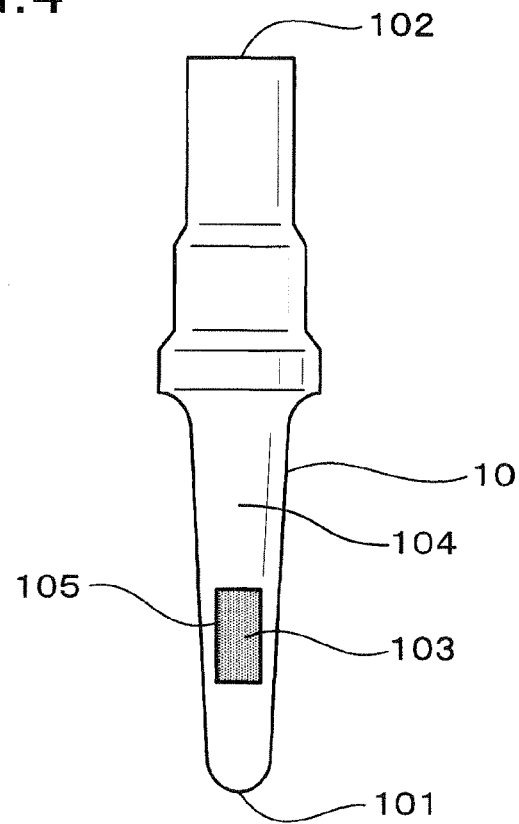
FIG. 4 is a side view of a basal body of the gas sensor element, the basal body having a solid electrolyte portion formed in part of a side wall thereof.

The green body 100 is then degreased in the degreasing step and further fired in the firing step. As a result, both the basal body 10 and the solid electrolyte portion 103 are obtained; they are integrally formed into one piece so that the solid electrolyte portion 103 is embedded in part of the side wall 104 of the basal body 10 as shown in FIG. 4.

In addition, the firing temperature, at which the green body 100 is fired, may be suitably set according to the compositions of the first and second clays 18 and 19.

In the electrode forming step, the reference and measurement electrodes 11 and 12 are respectively formed on the internal and external surfaces 106 and 107 of the basal body 10 by first electroless-depositing platinum on the surfaces 106 and 107 and then performing a heat treatment at, for example, 1000° C.

In addition, in the present embodiment, the porous protect layer 13 is further formed by plasma-spraying $MgO.Al_2O_3$ spinel so as to completely cover the electrode portion 121 of the measurement electrode 12.

As a result, the gas sensor element 1 according to the present embodiment is finally obtained.

In addition, the inventors of the present invention have conducted a non-contact measurement using a laser displacement meter to measure the difference in surface level between the basal body 10 and the solid electrolyte portion 103 at the boundary 105 therebetween. As a result, it has been made clear that the difference in surface level between the basal body 10 and the solid electrolyte portion 103 at the boundary 105 therebetween is 3 μm at most on both the internal surface 106 and external surface 107 of the basal body 10.

According to the present embodiment, it is possible to achieve the following advantages.

As described above, in the gas sensor element 1 according to the present embodiment, the solid electrolyte portion 103 is integrally formed with the basal body 10 so as to be embedded in part of the side wall 104 of the basal body 10. The difference in surface level between the basal body 10 and the solid electrolyte portion 103 at the boundary 105 therebetween is less than or equal to 30 μm, and more specifically 3 μm at most on both the internal surface 106 and external surface 107 of the basal body 10.

Consequently, during the firing process of the gas sensor element 1 or when thermal shock is applied to the gas sensor element 1 due to water contained in the measurement gas, stress concentration can be prevented from occurring at the boundary 105 between the basal body 10 and the solid electrolyte portion 103. As a result, it is possible to prevent cracks from occurring in the gas sensor element 1.

Moreover, in the gas sensor element 1 according to the present embodiment, the basal body 10 has the bottomed tubular shape. Therefore, unlike a plate-shaped gas sensor element, the gas sensor element 1 can be configured to have no corner portion at the measurement gas-side end thereof (i.e., at the closed end 101 of the basal body 10). Consequently, it is possible to prevent cracks from occurring in the gas sensor element 1 due to stress concentration at a corner portion thereof. In addition, it is also possible to prevent the gas sensor element 1 from being damaged during the assembly thereof with other components due to collision of a corner portion thereof against the other components.

In the gas sensor element 1 according to the present embodiment, the side wall 104 and bottom wall 108 of the basal body 10 are connected with each other via the curved boundary portion 148 therebetween. Consequently, it is possible to prevent stress concentration from occurring at the boundary portion 148 between the side wall 104 and bottom wall 108 of the basal body 10, thereby more reliably preventing cracks from occurring in the gas sensor element 1.

In the gas sensor element 1 according to the present embodiment, the basal body 10 contains alumina as its major component. Consequently, it is possible to secure both high heat conductivity and high electrical insulating properties of the basal body 10.

In the gas sensor element 1 according to the present embodiment, the solid electrolyte portion 103 contains the partially-stabilized zirconia as its major component. Consequently, it is possible to secure high sensitivity of the gas sensor element 1.

In the present embodiment, the method of manufacturing the gas sensor element 1 includes the first and second shaping steps and the firing step. In the first shaping step, the first clay 18, which is prepared for forming the basal body 10, is shaped into the bottomed tubular shape of the basal body 10 so that the void space 201 is formed in the shaped first clay 18 at the position corresponding to the solid electrolyte portion 103. In the second shaping step, the second clay 19, which is prepared for forming the solid electrolyte portion 103, is filled into the void space 201, thereby being shaped into the shape of the solid electrolyte portion 103. In the firing step, both the shaped first and second clays 18 and 19 are fired together to form the basal body 10 and the solid electrolyte portion 103.

With the above method, the basal body 10 and the solid electrolyte portion 103 can be integrally formed into one piece so that the solid electrolyte portion 103 is embedded in part of the side wall 104 of the basal body 10. Moreover, since the second clay 19 is shaped by being filled into the void space 201 previously formed in the first clay 18, it is possible to realize such a small difference in surface level between the basal body 10 and the solid electrolyte portion 103 at the boundary 105 therebetween as described above.

In the present embodiment, both the first and second clays 18 and 19 are shaped by injection molding using the die assembly 2. Consequently, it is possible to accurately shape both the first and second clays 18 and 19, thereby reliably suppressing the difference in surface level between the basal body 10 and the solid electrolyte portion 103 at the boundary 105 therebetween.

In the present embodiment, the die assembly 2 has the cavity 20 formed therein; the cavity 20 has the bottomed tubular shape of the basal body 10. In the first shaping step, the first clay 18 is filled into the cavity 20 with the portion 201 of the cavity 20 occupied by the movable die 231. In the second shaping step, the second clay 19 is filled into the void space 201 which is formed in the shaped first clay 18 by removing the movable die 231 to vacate the portion 201 of the cavity 20. Consequently, it is possible to easily form the basal body 10 and the solid electrolyte portion 103 integrally so that the solid electrolyte portion 103 is embedded in part of the side wall 104 of the basal body 10.

In the present embodiment, the method of manufacturing the gas sensor element 1 includes the degreasing step after the second shaping step and before the firing step. Consequently, by performing the degreasing step, it is possible to remove organic components included in the green body 100 before firing it.

In addition, in the gas sensor element 1 according to the present embodiment, there is only the single solid electrolyte portion 103 formed in the side wall 104 of the basal body 100 as described above. However, it is also possible to form more than one solid electrolyte portion 103 in the side wall 104 of the basal body 10. Moreover, it is also possible to form one or more solid electrolyte portion 103 in the bottom wall 108 of the basal body 10.

Figure 11:
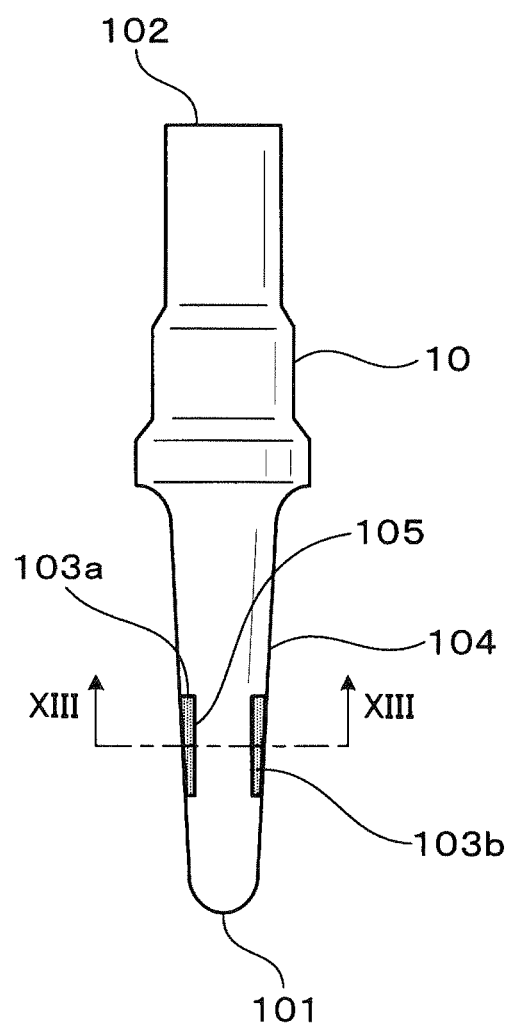
FIG. 11 is a side view of a basal body according to a first modification, wherein a pair of solid electrolyte portions is formed in a side wall of the basal body.
Figure 12:
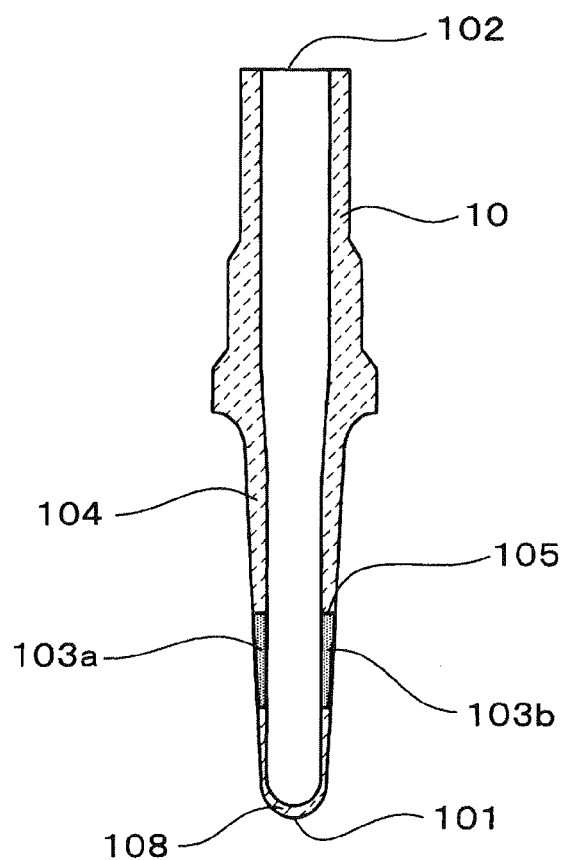
FIG. 12 is a cross-sectional view of the basal body of FIG. 11 taken along the longitudinal direction of the basal body.
Figure 13:
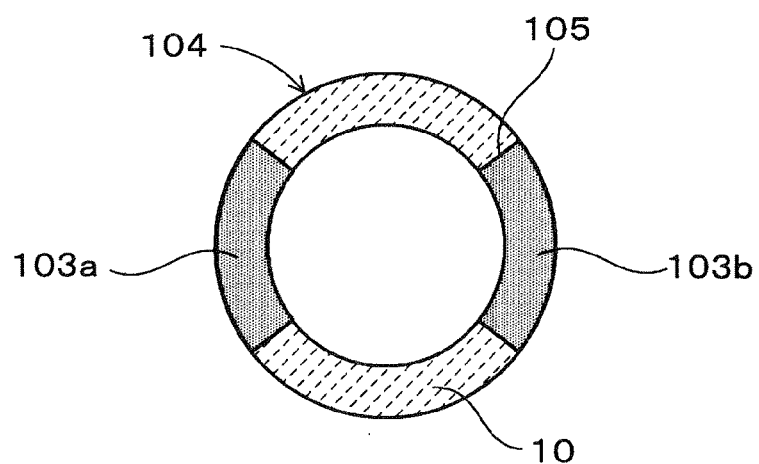
FIG. 13 is a cross-sectional view of the basal body taken along the line XIII-XIII in FIG. 11.

For example, in a first modification as shown in FIGS. 11-13, there is a pair of solid electrolyte portions 103a and 103b formed in the side wall 104 of the basal body 10. The solid electrolyte portions 103a and 103b are positioned close to the closed end 101 of the basal body 10 and opposed to each other with the hollow space of the basal body 10 interposed therebetween.

Figure 14:
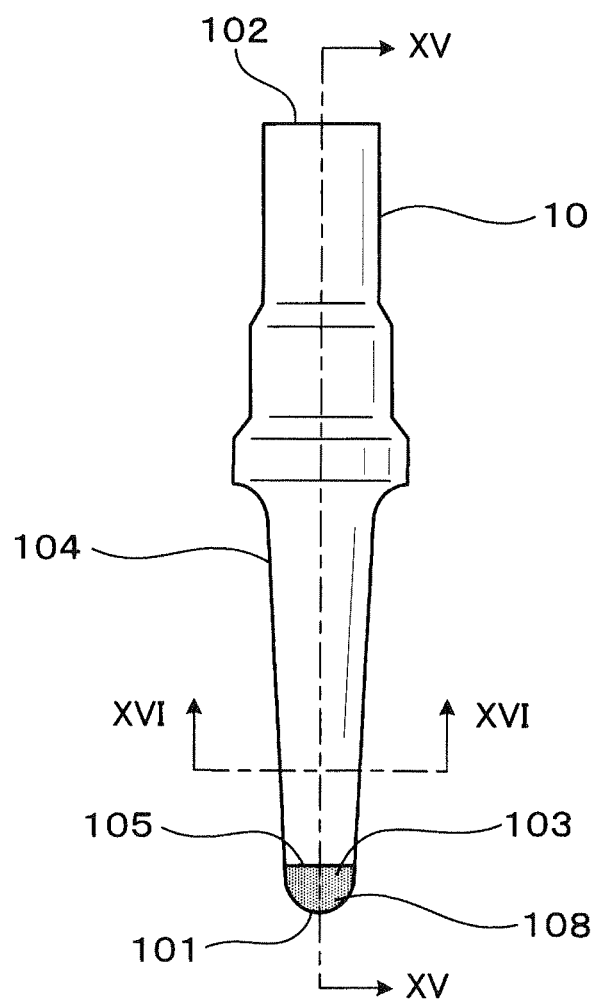
FIG. 14 is a side view of a basal body according to a second modification, wherein a solid electrolyte portion is formed in the basal body so as to replace the whole of a bottom wall of the basal body.
Figure 15:
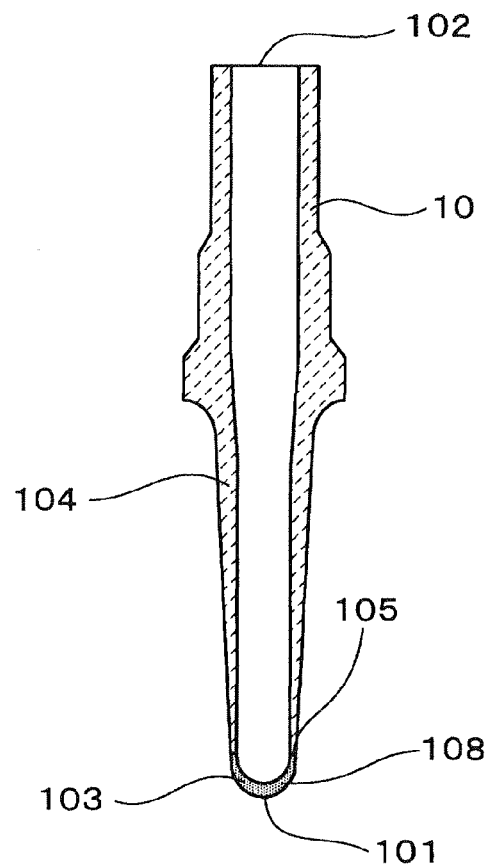
FIG. 15 is a cross-sectional view of the basal body taken along the line XV-XV in FIG. 14.
Figure 16:
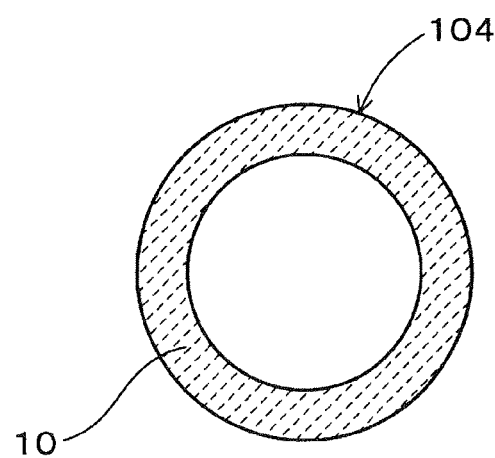
FIG. 16 is a cross-sectional view of the basal body taken along the line XVI-XVI in FIG. 14.

In a second modification as shown in FIGS. 14-16, there is one solid electrolyte portion 103 formed in the basal body 10 so as to replace the entire bottom wall 108 of the basal body 10.

Figure 17:
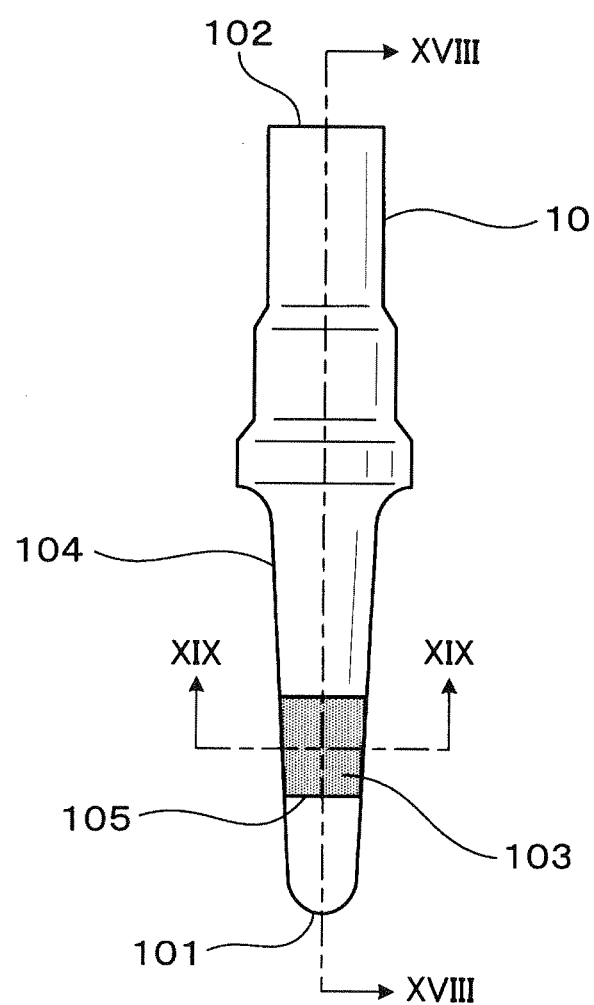
FIG. 17 is a side view of a basal body according to a third modification, wherein a solid electrolyte portion is formed in part of a side wall of the basal body over the entire circumference of the side wall.
Figure 18:
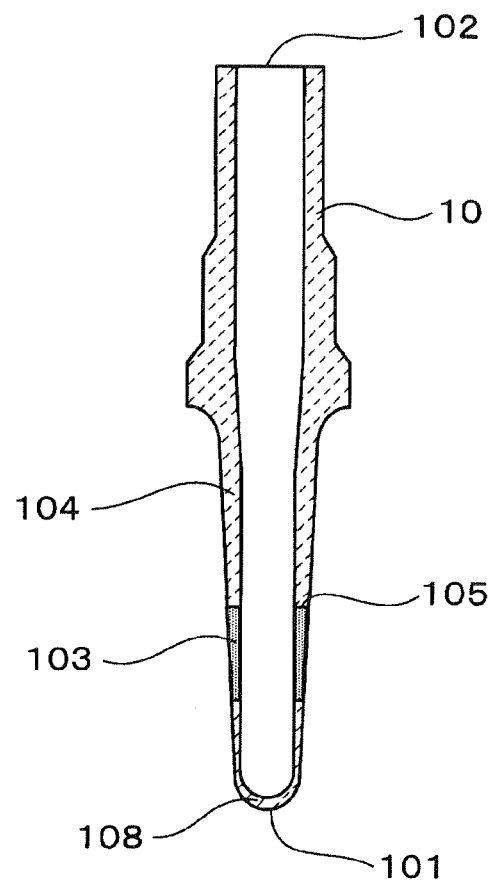
FIG. 18 is a cross-sectional view of the basal body taken along the line XVIII-XVIII in FIG. 17.
Figure 19:
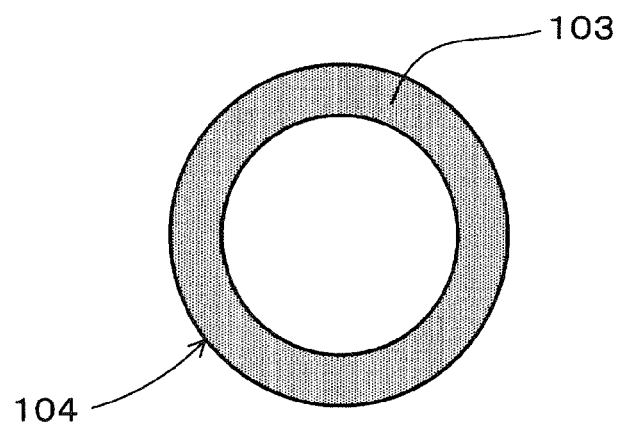
FIG. 19 is a cross-sectional view of the basal body taken along the line XIX-XIX in FIG. 17.

In a third modification as shown in FIGS. 17-19, there is one solid electrolyte portion 103 formed in the side wall 104 of the basal body 10 over the entire circumference of the side wall 104. In addition, the solid electrolyte portion 103 replaces only part of the side wall 104 of the basal body 10 in the vicinity of the closed end 101 of the basal body 10.

Figure 20:
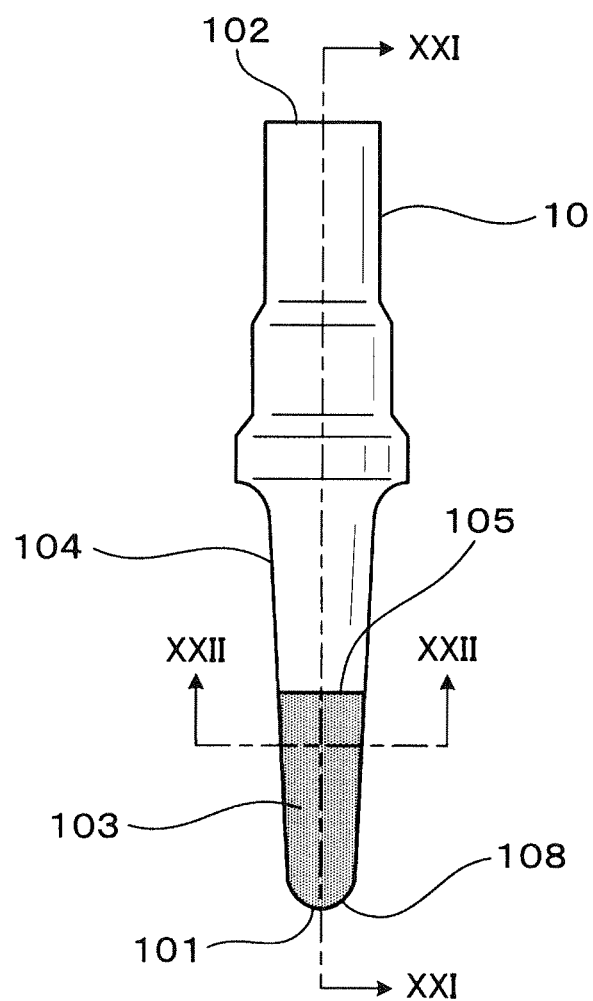
FIG. 20 is a side view of a basal body according to a fourth modification, wherein a solid electrolyte portion is formed in the basal body so as to replace the whole of a bottom wall of the basal body as well as part of a side wall of the basal body.
Figure 21:
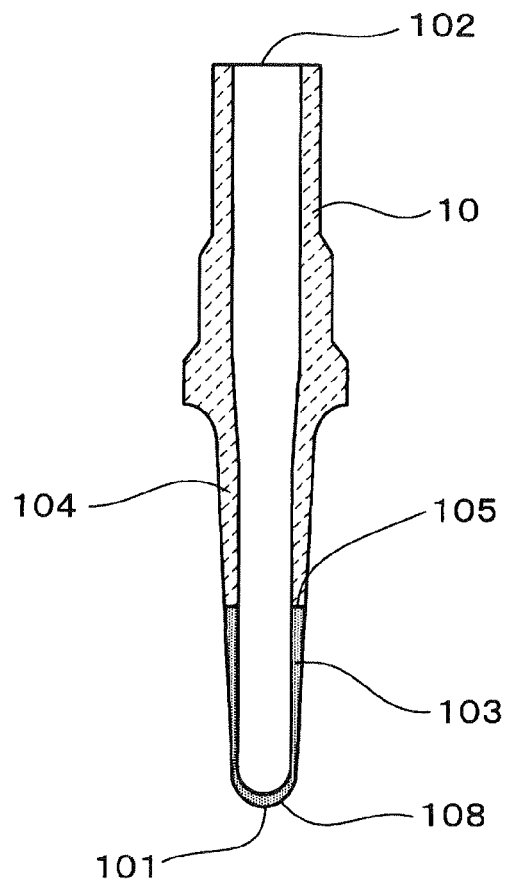
FIG. 21 is a cross-sectional view of the basal body taken along the line XXI-XXI in FIG. 20.
Figure 22:
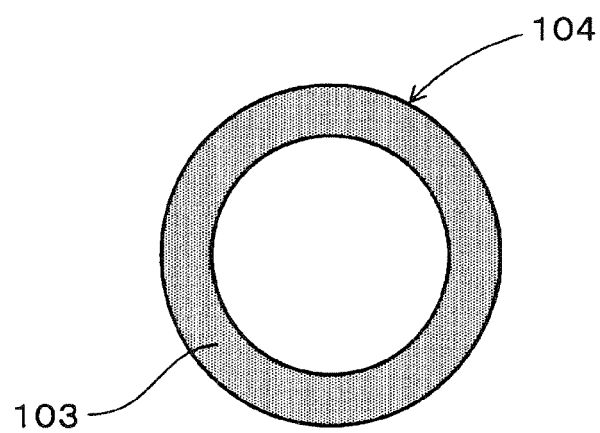
FIG. 22 is a cross-sectional view of the basal body taken along the line XXII-XXII in FIG. 20.

In a fourth modification as shown in FIGS. 20-22, there is one solid electrolyte portion 103 formed in the basal body 10 so as to replace the entire bottom wall 108 of the basal body 10 as well as part of the side wall 104 of the basal body 10 which adjoins the bottom wall 108. In addition, the solid electrolyte portion 103 is formed in the side wall 104 of the basal body 10 over the entire circumference of the side wall 104.

It should be noted that in the above-described first to fourth modifications, the solid electrolyte portions may also be integrally formed with the basal body 10 by injection molding so that the differences in surface level between the solid electrolyte portions and the basal body 10 at the boundaries therebetween are 3 μm at most.

Second Embodiment

This embodiment illustrates a gas sensor element 3 which has a similar configuration to the gas sensor element 1 according to the first embodiment. Accordingly, only the differences between the gas sensor elements 1 and 3 will be described hereinafter.

In the first embodiment, the gas sensor element 1 is configured to be used in a lambda sensor. The gas sensor element 1 includes, in addition to the basal body 10, the solid electrolyte portion 103 and the reference and measurement electrodes 11 and 12, the porous protective layer 13 that is formed on the measurement electrode 12 so as to completely cover the electrode portion 121 of the measurement electrode 12.

Figure 23:
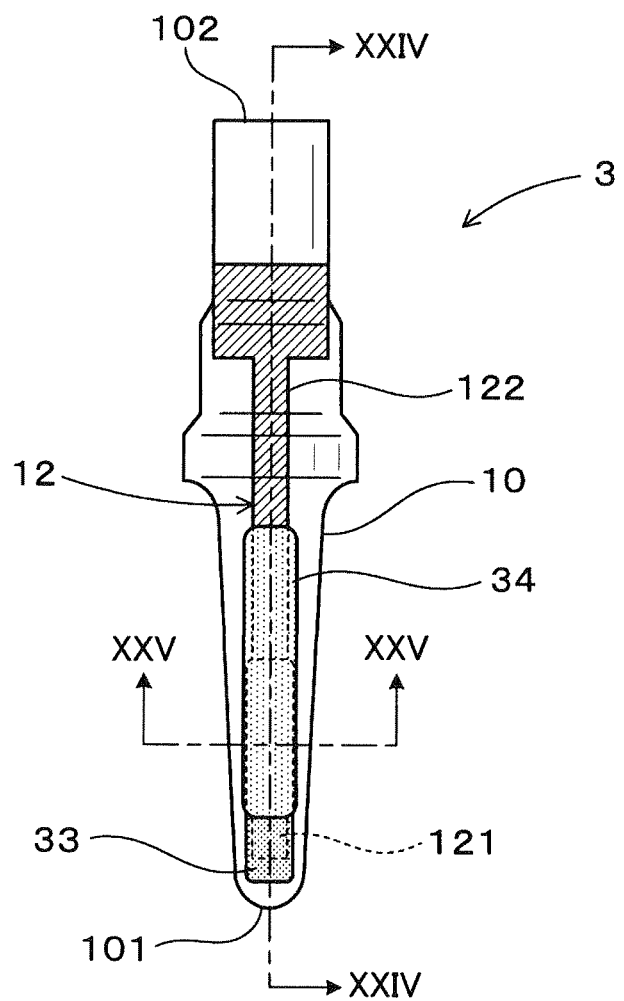
FIG. 23 is a side view of a gas sensor element according to a second embodiment.
Figure 24:
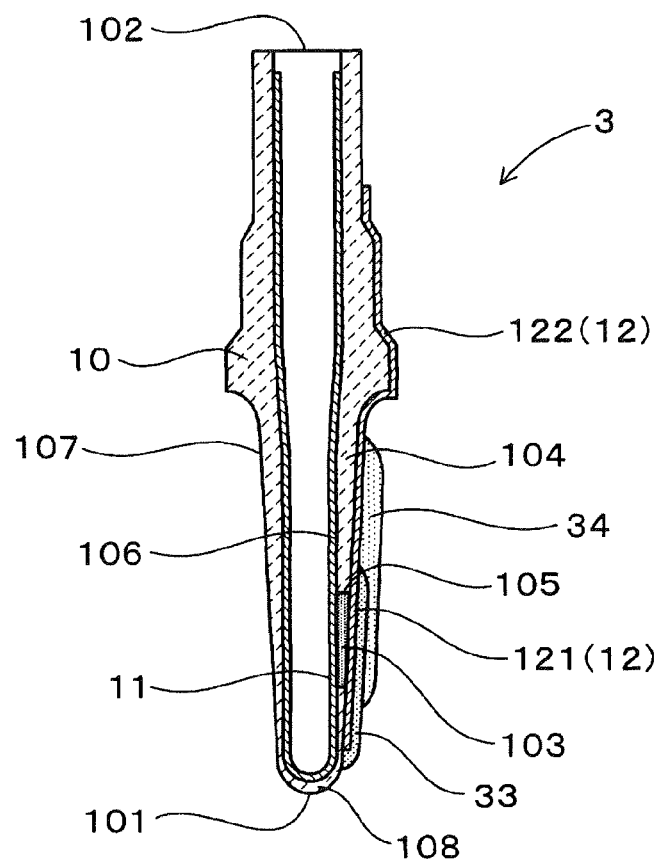
FIG. 24 is a cross-sectional view of the gas sensor element taken along the line XXIV-XXIV in FIG. 23.
Figure 25:
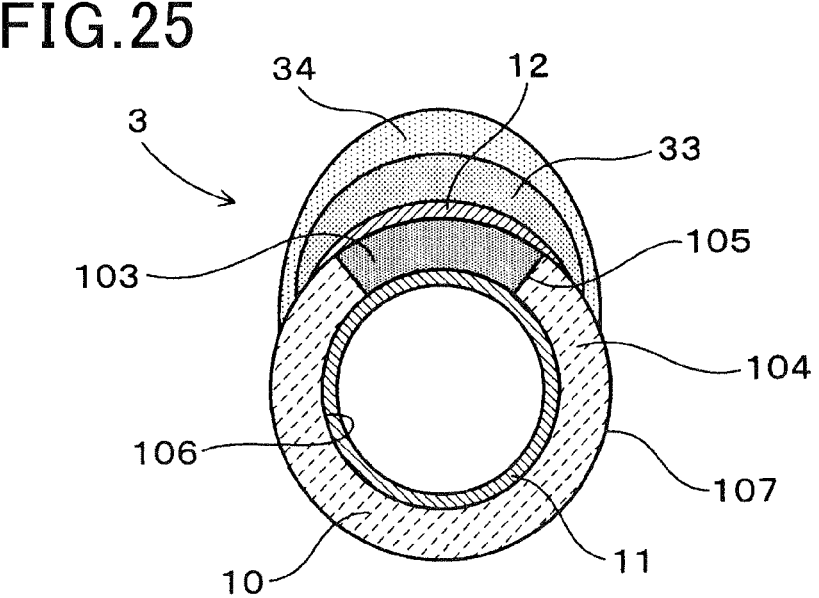
FIG. 25 is a cross-sectional view of the gas sensor element taken along the line XXV-XXV in FIG. 23.

In comparison, in the present embodiment, the gas sensor element 3 is configured to be used in an A/F ratio sensor. As shown in FIGS. 23-25, the gas sensor element 3 includes a diffusion-resistant layer 33 and a shield layer 34 in addition to the basal body 10, the solid electrolyte portion 103 and the reference and measurement electrodes 11 and 12. In other words, the gas sensor element 3 includes the diffusion-resistant layer 33 and the shield layer 34 instead of the porous protective layer 13 included in the gas sensor element 1 according to the first embodiment.

More specifically, in the gas sensor element 3 according to the present embodiment, the diffusion-resistant layer 33 is formed on the measurement electrode 12 so as to completely cover the electrode portion 121 of the measurement electrode 12. The diffusion-resistant layer 33 is made of a porous refractory metal oxide, such as porous $MgO \cdot Al_2O_3$ spinel. The diffusion-resistant layer 33 has a predetermined porosity so as to control diffusion of the measurement gas.

The shield layer 34 is formed on the diffusion-resistant layer 33 so as to only partially cover the diffusion-resistant layer 33. More specifically, part of the diffusion-resistant layer 33 on the side of the closed end 101 of the basal body 10 is not covered by the shield layer 34. The shield layer 34 is made of a nonporous (or dense) refractory metal oxide, such as nonporous $MgO \cdot Al_2O_3$ spinel. Therefore, the shield layer 34 is impermeable to the measurement gas.

Consequently, in operation of the gas sensor element 3, the measurement gas flows into the diffusion-resistant layer 33 from only that part of the diffusion-resistant layer 33 which is not covered by the shield layer 34, and further flows to the electrode portion 121 of the measurement electrode 12 through the inside of the diffusion-resistant layer 33.

The gas sensor element 3 according to the present embodiment has the same advantages as the gas sensor element 1 according to the first embodiment.

While the above particular embodiments and modifications have been shown and described, it will be understood by those skilled in the art that various further modifications, changes, and improvements may be made without departing from the spirit of the invention.

For example, in the first embodiment, both the first clay 18 for forming the basal body 10 and the second clay 19 for forming the solid electrolyte portion 3 are shaped by injection molding using the die assembly 2. However, it is also possible to shape the first and second clays 18 and 19 by other methods, for example by slipcasting using a gypsum mold or a resin mold.

What is claimed is:

1. A method of manufacturing a gas sensor element, wherein the gas sensor element comprises:
   a basal body that has a bottomed tubular shape and is made of an electrically insulative ceramic material, the basal body having a side wall and a bottom wall;
   at least one solid electrolyte portion formed in the bottom wall or the side wall of the basal body; and
   a pair of electrodes that are opposed to each other with the at least one solid electrolyte portion interposed therebetween,
   the method comprising the sequential steps of:
   shaping a first clay, which is provided for forming the basal body, into the bottomed tubular shape of the basal body so that at least one void space is formed in the shaped first clay;
   shaping a second clay, which is provided for forming the at least one solid electrolyte portion, into a shape of the at least one solid electrolyte portion by filling the second clay into the at least one void space formed in the shaped first clay;
   firing both the shaped first and second clays together to form the basal body and the at least one solid electrolyte portion; and
   forming the pair of electrodes respectively on opposite sides of the at least one solid electrolyte portion, wherein
   both the first and second clays are shaped by injection molding using a single die assembly,
   the die assembly has a cavity formed therein,
   the cavity having the bottomed tubular shape of the basal body,
   in the first clay shaping step, the first clay is filled into the cavity with at least one portion of the cavity occupied by a movable member, and
   in the second clay shaping step, the second clay is filled into the at least one void space which is formed in the shaped first clay by removing the movable member to vacate the at least one portion of the cavity.

2. The method as set forth in claim 1, further comprising, after the second clay shaping step and before the firing step, a step of degreasing both the shaped first and second clays.

* * * * *